(12) United States Patent
Schomburg et al.

(10) Patent No.: US 7,822,475 B2
(45) Date of Patent: Oct. 26, 2010

(54) METHOD AND APPARATUS FOR REDUCING FAR-FIELD INTERCHAMBER INTERFERENCE IN AN IMPLANTED MEDICAL DEVICE

(75) Inventors: Richard A. Schomburg, Hillsboro, OR (US); Christopher S. de Voir, Tigard, OR (US); Dirk Muessig, West Linn, OR (US)

(73) Assignee: Biotronik CRM Patent AG (CH)

( * ) Notice: Subject to any disclaimer, the term of this patent is extended or adjusted under 35 U.S.C. 154(b) by 1599 days.

(21) Appl. No.: 11/015,561

(22) Filed: Dec. 17, 2004

(65) Prior Publication Data
US 2005/0165455 A1 Jul. 28, 2005

Related U.S. Application Data

(60) Provisional application No. 60/530,380, filed on Dec. 17, 2003, provisional application No. 60/533,657, filed on Dec. 30, 2003.

(51) Int. Cl.
*A61N 1/365* (2006.01)
(52) U.S. Cl. .......................... 607/27; 600/510
(58) Field of Classification Search .................. 607/27; 600/509–510, 514–518
See application file for complete search history.

(56) References Cited

U.S. PATENT DOCUMENTS

| | | | | |
|---|---|---|---|---|
| 4,537,200 A | * | 8/1985 | Widrow | 600/509 |
| 4,799,486 A | | 1/1989 | DuFault | |
| 4,799,493 A | * | 1/1989 | DuFault | 600/518 |
| 4,907,248 A | * | 3/1990 | Bretl | 375/244 |
| 5,300,093 A | * | 4/1994 | Koestner et al. | 607/32 |
| 5,755,739 A | * | 5/1998 | Sun et al. | 607/14 |
| 5,776,072 A | * | 7/1998 | Hsu et al. | 600/518 |
| 5,983,127 A | * | 11/1999 | dePinto | 600/509 |
| 6,275,591 B1 | * | 8/2001 | Hsueh et al. | 381/71.11 |
| 2003/0050563 A1 | * | 3/2003 | Suribhotla et al. | 600/509 |
| 2003/0199939 A1 | | 10/2003 | Schmitt et al. | |

* cited by examiner

*Primary Examiner*—George R Evanisko
*Assistant Examiner*—Rex Holmes
(74) *Attorney, Agent, or Firm*—Hahn, Loeser & Parks, LLP

(57) ABSTRACT

An implantable medical device comprises at least two sensing channels for receiving sensed first and second location electrical signals originating from two different locations of a heart. A control unit is connected to the sensing channels and is adapted to process sensed electrical signals originating from first and second locations of the heart. The control unit incorporates an adaptive filter compensator adapted to generate an estimate signal for compensating a far-field contribution of the second location signal to the first location signal, thereby generating an output signal representing a near field signal originating from the first location. A gate is connected to the second location sensing channel and is adapted to enable the adaptive filter compensator only if a predetermined signal is sensed via the second location sensing channel.

14 Claims, 10 Drawing Sheets

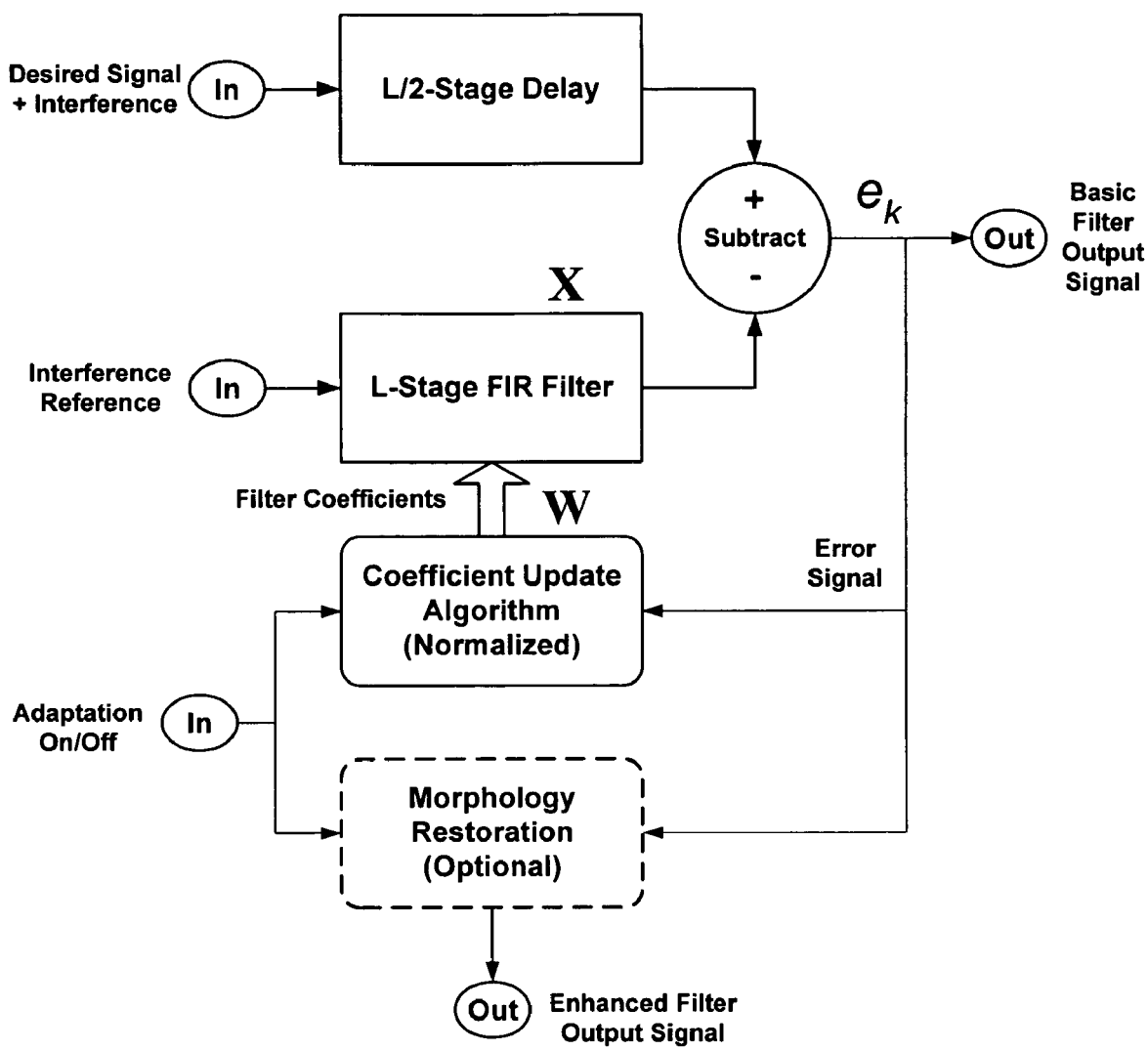
Fig. 1: Adaptive Filter Block Diagram
W = vector of FIR coefficients
X = vector of FIR values
k = sample number
µ = update step size
L = FIR filter length
e = update error signal
Normalized LMS Update Algorithm:
$$W_{k+1} = W_k + \mu \frac{e_k X_k}{\sum_{m=1}^{L} x_{m,k}^2}$$

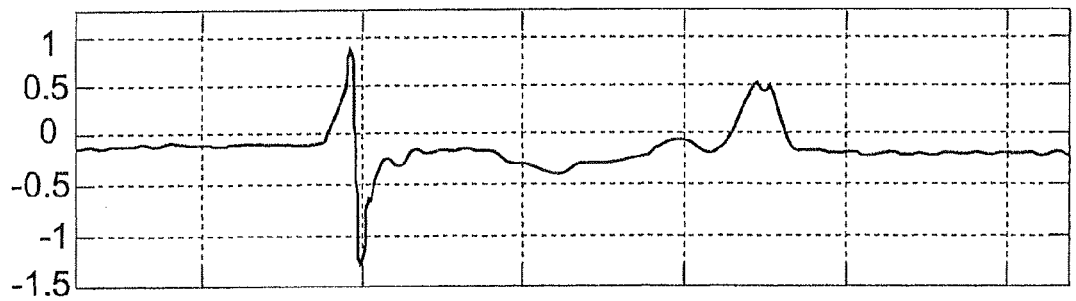
Fig.2a Atrial IEGM with crosstalk
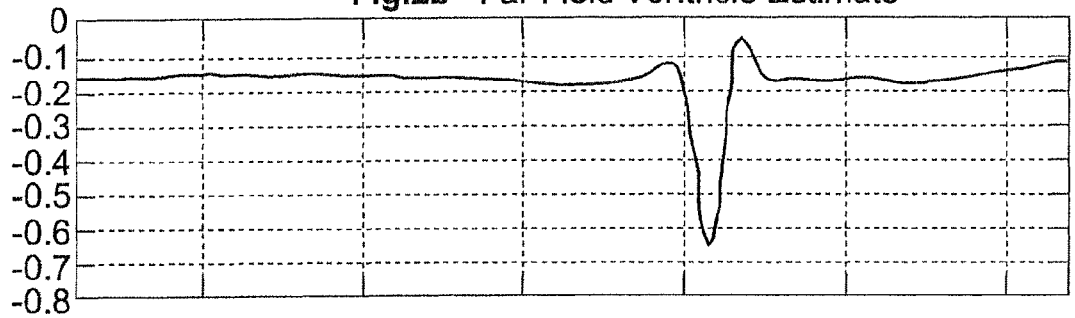
Fig.2b Far Field Ventricle Estimate
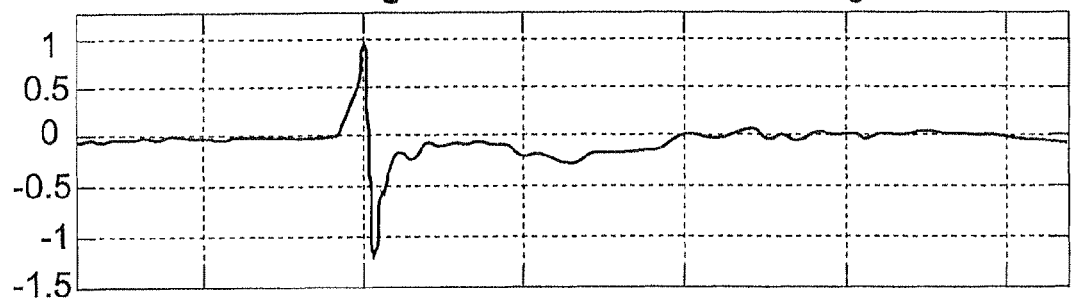
Fig.2c Post-Processed Atrial Signal
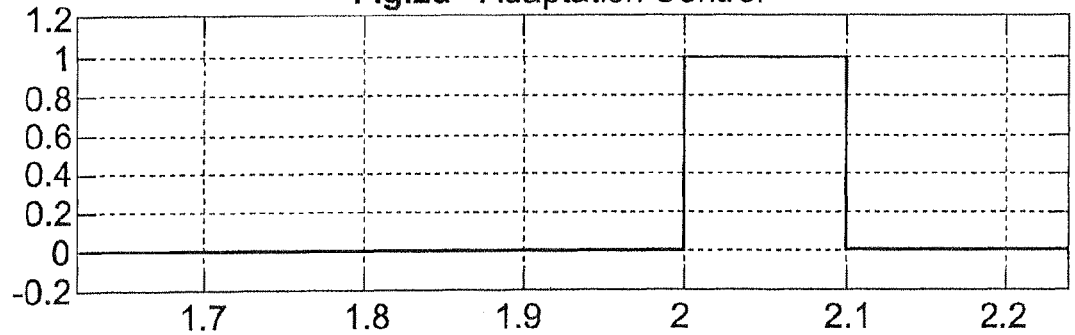
Fig.2d Adaptation Control
Fig.2 Adaptive Filter Waveforms

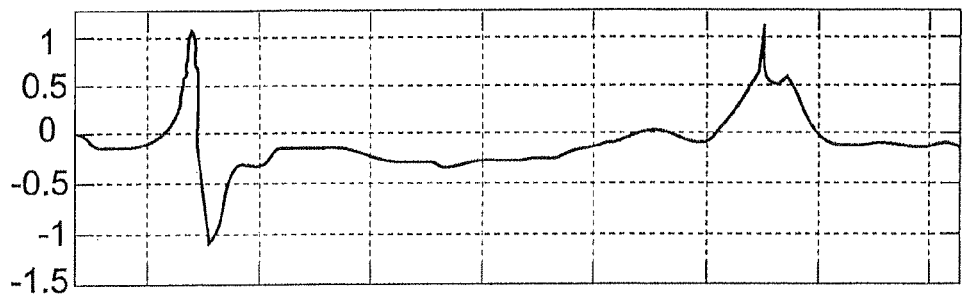
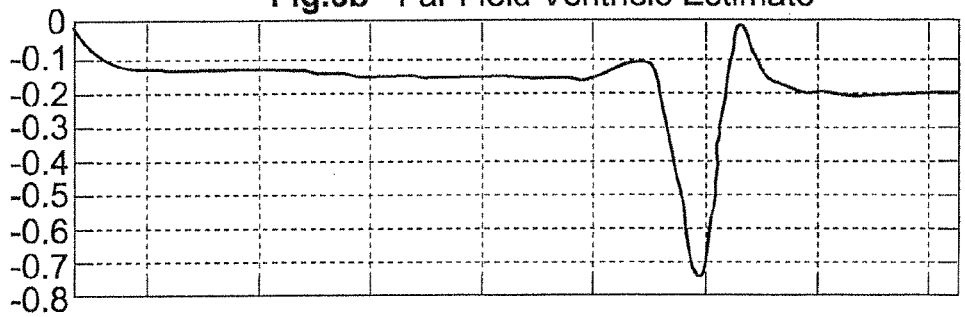
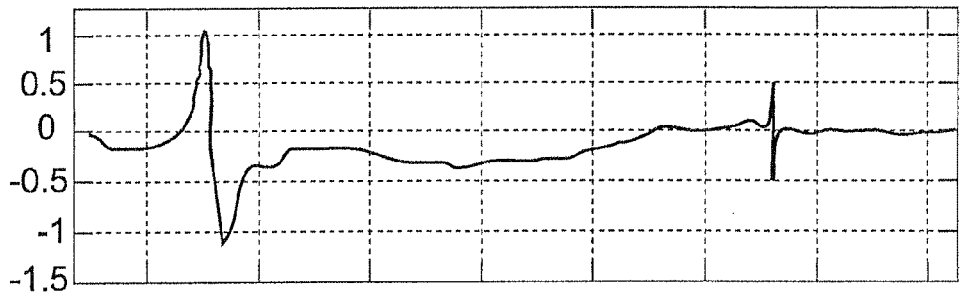
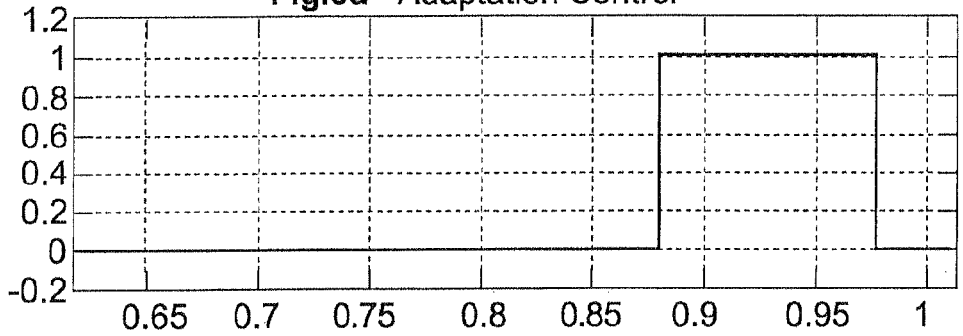
Fig.3

Fig. 4: Far-Field Interference Reduction Example

Fig. 5: Instability Occurrence in an Adaptive Filter

Fig. 7: A General Adaptive Filter Algorithm function [lmsOut, errCode] = lmsFilter(signal, noise, adapt, firLen, mu, alpha, nMode, rMode)
% Vector-based LMS adaptive filter with gated adaptation
% Revision 4    28 August 2003    R. A. Schomburg % Input vector 'signal' is the N-sample signal+noise time series
% Input vector 'noise' is the N-sample interference reference
% Input vector 'adapt' is the N-sample adaptation control sequence:
%    1 = adaptation ON, 0 = adaptation OFF, sample-by-sample
%    Note: If length(adapt) is unity, adaptation is ON for all samples
% Input scalar 'firLen' is the length of the adaptive filter, and must be even
% Input scalar 'mu' is the adaptation stepsize control parameter
% Input scalar 'alpha' is the adaptation leakage parameter, in range 0..1
% Input scalar 'nMode' is the LMS normalization control parameter,
%    nMode == -1 enables Nagumo&Noda algorithm with sum-of-|P| normalization
%    nMode == 0 disables LMS normalization (update equation denominator = 1)
%    nMode == 1 enables LMS sum-of-squares (traditional) normalization,
%    nMode >= 2 enables LMS nSqrMax, with multiplier n equal to the nMode value
% Input scalar 'rMode' is the morphology restoration control parameter,
%    0=OFF, 1=ON, integrates output during adaptation
% Output vector 'lmsOut' is the N-sample output of the adaptive filter
% Output scalar 'errCode' reports the processing result:
%    0 = normal, +1 = noise array size error, +2 = adapt array size error,
%    +4 = adaptation sequence error, +8 =odd firLen, +16 = algorithm diverges N = length(signal);        % count the number of signal samples
sigPeak = max(abs(signal));   % peak signal value, used in alg divergence test % Initialize and (as needed) increment the errCode, based on input arguments:
errCode = 0;
% test the noise array length:
if length(noise) ~= N, errCode = errCode + 1; end
% test the adapt array length (if adapt length > 1):
if (length(adapt) > 1) & (length(adapt) ~= N), errCode = errCode + 2; end
% check for an unterminated adaptation sequence (if adapt length > 1):
if (length(adapt) > 1) & (adapt(N) == 1), errCode = errCode + 4; end
% check for an odd firLen:
if mod(firLen,2) == 1, errCode = errCode + 8; end % Mandatory return on a non-zero errCode:
if errCode ~= 0
   lmsOut = 0; % return zero on errors 0..15
   return

Fig. 7 (continued)

```
end

% Pre-define the working arrays (this reduces function processing time):
if length(adapt) == 1, adaptOn = ones(N,1);   % sets full-time adaptation,
else adaptOn = adapt;   % or uses the input argument (a specific gating pattern)
end
lmsOut = zeros(N,1);    % initialize the output sequence
h = zeros(firLen,1);    % initialize the filter coefficient array
p = zeros(firLen,1);    % initialize the noise reference array % Construct the causal-delayed (firLen/2) version of the signal vector;
% the adapt vector is also delayed to retain synchrony with the signal.
delayLine = zeros(firLen/2,1);   % define the delayline coefficients,
delayLine(end) = 1;       % all zeroes except the final value
dlySignal = filter(delayLine,1,signal); % the delayed input signal
dlyAdapt = filter(delayLine,1,adaptOn); % the delayed adaptation signal for i = 2:N
    p(1) = noise(i);   % load the i-th noise reference sample into p(1)
    firOut = 0;        % initialize the FIR filter output value % calculate the normalization factor
    if nMode == -1, normFactor = 1e-10 + sum(abs(p)); end        % Nagumo&Noda
    if nMode == 0, normFactor = 1; end                            % LMS
    if nMode == 1, normFactor = 1e-10 + sum(p.*p); end            % LMS
    if nMode >= 2, normFactor = 1e-10 + nMode*max(abs(p))^2; end  % LMS % calculate the FIR filter output
    for k = 1:firLen
        firOut = firOut + p(k)*h(k);
    end % force a return on algorithm divergence
    if (firOut > 10*sigPeak)|(isnan(firOut))
        errCode = errCode + 16;        % increment the error code
        lmsOut = i;                    % return sample number if divergent
        i = N;                         % inhibit further processing of 'signal'
        return
    end
        % calculate the system error signal
    errSig = dlySignal(i) - firOut;   % subtract FIR output from input signal % if using morphology restoration, capture the pre-adaptation lmsOut value
```

Fig. 7 (continued)

```
if (rMode == 1)&(dlyAdapt(i) > dlyAdapt(i-1))   % if at start of an adaptation zone
    restoreInit = lmsOut(i-1);   % save the previous output value
end % calculate the new FIR coefficients and update the system output
if dlyAdapt(i) == 1   % if adaptation is specified for this sample,
    for k = 1:firLen   % update the FIR coeficients
        if nMode >= 0, h(k) = h(k)*alpha + p(k)*2*mu*errSig/normFactor; end
        if nMode ==-1, h(k) = h(k)*alpha + sign(p(k))*mu*errSig/normFactor; end
    end
    if rMode == 1
        lmsOut(i) = restoreInit + errSig;
%       lmsOut(i) = lmsOut(i-1) + errSig;
    else
        lmsOut(i) = errSig;
    end
else   % this group of samples-with-adaptation is now processed, so
    h = zeros(firLen,1);   % re-initialize the filter coefficients
    lmsOut(i) = errSig;
end for k = 1:firLen-1
    p(firLen-k+1) = p(firLen-k);   % right-shift the noise reference
end   % now ready to update p(1) on next pass around this FOR loop
end
```

METHOD AND APPARATUS FOR REDUCING FAR-FIELD INTERCHAMBER INTERFERENCE IN AN IMPLANTED MEDICAL DEVICE

CROSS-REFERENCE TO RELATED APPLICATIONS

This application claims priority from U.S. Provisional Patent Application No. 60/530,380 filed on Dec. 17, 2003 and U.S. Provisional Patent Application No. 60/533,657 filed on Dec. 30, 2003.

BACKGROUND OF THE INVENTION

The invention relates to a method for use in association with an implanted medical device, particularly a device for performing cardiac pacing, defibrillation, cardioversion and the like. Such devices require the concurrent observation and interpretation of intracardiac electrogram (IEGM) signals that are obtained from multiple cardiac chambers. The method of the invention involves a signal, processing technique for reducing the interference of the signals.

The existence and use of implanted medical devices to conduct cardiac electrotherapy, including, for illustrative purposes, cardiac pacing, defibrillation, cardioversion and the like, is well-known. These devices rely upon a reliable technique for monitoring and analyzing the underlying electrical activity of the heart, as it is precisely this activity which may be therapeutically affected by the device. In the majority of these devices, the device receives signals from more than one of the cardiac chambers. Proper monitoring and analysis can be greatly enhanced if a single signal may be considered the exclusive representation of activity in the chamber from which the signal is detected. In other words, it is highly desirable to be able to consider a detected signal as being indicative of "near field" electrical activity.

In actual practice, the signal originating in a chamber cannot be reliably considered to be the exclusive representation of activity in that chamber. Several factors are responsible for this, including the details of implant lead placement, an inherent disparity of signal amplitudes, and other reasons.

A particular problem is the problem of "crosstalk" between chambers, that is, the interpretation of a signal not originating in a chamber as a signal that has originated in the chamber. Most commonly, this crosstalk is characterized by the misinterpretation of an electrical signal arising in a ventricle as an atrial signal, through detection of the signal in the atrial IEGM. When this happens, the resultant electrotherapy errors may be both errors of commission and omission. This crosstalk is also referred to as "far field" interference, as it is indicative of "far field" electrical activity.

From the prior art techniques known to the inventors of the present invention, this misinterpretation of signals due to crosstalk has been reduced by using a blanking technique, whereby a signal channel (usually an atrial signal channel) is desensitized during a portion of a cardiac cycle when the crosstalk interference could occur. The unfortunate consequence of this technique is the fact that legitimate signals originating during the blanking period in the chamber in which the signal is blanked are simply not observed, and cannot be acted upon. This compounds the difficulty of properly interpreting the conditions in the heart and particularly in the chamber in which the signal has been blanked.

A more advanced technique is disclosed in U.S. Pat. No. 4,799,486. U.S. Pat. No. 4,799,486 discloses a method and an apparatus for suppressing the ventricular component from an atrial sensing lead used with a dual chamber cardiac pacer, thus obviating the need for an atrial sense refractory period to prevent oversensing of the ventricular interference. The apparatus according to U.S. Pat. No. 4,799,486 utilizes an adaptive filter embodying the Widrow-Hoff least mean square (LMS) algorithm which is connected to receive signals from an endocardial lead having a bipolar ventricular electrode and a unipolar atrial electrode. The bipolar electrodes disposed in the ventricle are connected as the "input" $X_k$ signal to the LMS adaptive filter while the unipolar atrial electrode output is connected as the "desired" or reference signal $d_k$. In accordance with the LMS algorithm, the "error" signal is fed back and used to adjust the tap weights of the adaptive linear filter until the output thereof closely approximates the "desired" signal and then the "error" signal becomes a good approximation of the atrial signal alone, without the ventricular depolarization signal.

The apparatus according to U.S. Pat. No. 4,799,486 does require a considerable amount of the limited resources, in particular energy resources provided by an implantable medical device.

Therefore the object of the present invention is to provide a method and device where interchamber interference, and, particularly, ventricle to atrium crosstalk interference, can be significantly reduced while allowing full-time observation of chamber signals, particularly, atrial chamber signals, thereby only requiring minimized resources.

SUMMARY OF THE INVENTION

That object and others are achieved by an implantable medical device having at least two sensing channels for receiving sensed first and second location electrical signals originating from two different locations of a heart and a control unit being connected to said sensing channels and being adapted to process sensed electrical signals originating from first and second locations of a heart, wherein the control unit incorporates an adaptive filter compensator adapted to generate an estimate signal for compensating a far-field contribution of the second location signal to the first location signal, thereby generating an output signal representing a near field signal originating from the first location. According to the invention, a gate is provided which is connected to the second location sensing channel and which is adapted to enable the adaptive filter compensator only if a predetermined signal is sensed via the second location sensing channel.

The estimate signal generated by the adaptive filter compensator is subtracted from the first location sensed signal thereby generating the output signal representing a near field signal originating from the first location.

As already pointed out, the signal usually called an "error" signal is the signal to be used as the signal best representing the first location near field signal.

Gating the filter adaptation operation, i.e., so that it is activated only as needed in response to detected activity in the interfering chamber, effectively reduces the computational workload within an implant device.

Preferably, the gate is adapted to enable the adaptive filter compensator for a predetermined period of time. Said period of time adjusted to match the duration of the longest occurring QRS or QRST complex. Enabling the adaptive filter compensator for a predetermined period of time has proven to be an efficient means for saving resources of the implantable device.

In a preferred embodiment, the adaptive filter compensator comprise a L-stage least mean square (LMS) adaptive finite impulse response (FIR) filter. The signal resulting from subtracting the LMS adaptive filter output signal from the first location sensed signal is the signal usually called "error" signal, which is used for adoption of filter coefficients and as the signal representing a near field signal originating from the first location.

In a most interesting embodiment, the first location electrical signal is an atrial signal and the first sensing channel is an atrial sensing channel. In such embodiment, the first sensing channel is adapted to be connected to an intracardiac electrode lead having an atrial sensing electrode to be placed in an atrium of a heart. The second location electrical signal is a ventricular signal and the second sensing channel is a ventricular sensing channel. The second sensing channel is adapted to be connected to an intracardiac electrode lead having a ventricular sensing electrode to be placed in a ventricle of a heart.

Such an implantable medical device can be a dual chamber cardiac pacemaker or defibrillator sensing in the right ventricle and the right atrium.

Alternatively, the first and the second sensing channels may be a right ventricle sensing channel and a left ventricular sensing channel of a biventricular implantable medical device. In a similar manner, multiple chamber devices having sensing channels for up to all four chambers of a heart can be realized.

In a biventricular implantable medical device, the far-field contribution of the second location signal to the first location signal to be compensated is a far-field QRS signal originating from a ventricle and is sensed via the atrial channel and that the adaptive filter compensator is adapted to generate a compensation signal being approximately inverse to the far-field QRS signal sensed via the atrial channel.

Preferably, the adaptive filter compensator has an input for an noise reference input signal to be processed for generating the compensation signal, said noise reference input signal being the ventricular sensing signal. The underlying idea is to the far-field ventricular signal sensed in the atrium as "noise" with respect to the pure atrial near field signal emerging from the atrium itself. In such embodiment, it has proven beneficial to preprocess the noise reference input signal prior to processing by the adaptive filter compensator. Therefore, a preferred embodiment comprises such a preprocessor for pre-processing the noise reference input signal. Pre-processing of the ventricular noise-reference input signal $X_k$ (see FIG. 2) serves to better approximate the actual (interfering) ventricle signal waveform as seen at the atrial lead. This pre-processing step can reduce the system complexity, and reduce computational workload for a given level of system performance. Preferably, the preprocessor for pre-processing the noise reference input signal comprises a fixed coefficient FIR filter The resulting filter output "Atrial Detect Signal" (see FIG. 2) is nominally the first derivative of the atrial input signal, and thus exhibits a predictably different morphology, than the atrial input signal. Therefore, a preferred device includes a means to restore the original morphology after adaptive-filter reduction of the interchamber interference, as will be disclosed in more detail later herein.

In order to avoid instability of the least-mean-square filter coefficient update algorithm, the adaptive filter compensator comprises a L-stage least mean square filter which is connected to a filter coefficient updater which comprises a step size normalizer. Without this, the LMS algorithm is prone to instability and divergence within a changing signal environment, and is therefore less suited for use in a medical device providing life support functions. It is noted, the implantable medical device comprising a step size normalizer represents an invention which can be realized independently of any gate.

However, an implantable medical device comprising both, a gate and a step size normalizer, provides an additional advantage, namely, that the step size normalizer means can be optimised for compensating only a part of the sensed signal.

Alternative step-size normalizers may be provided in different, equally preferred embodiments, as disclosed in the following detailed description of preferred embodiments. Also, alternative filter coefficient updates can be provided, which can effectively reduce the computational workload within an implant device.

In a preferred embodiment, the control unit is adapted to determine a new set of actual coefficients which determine the operation of the adaptive filter compensator, for each actual event in the second location sensed signal. The implantable medical device according to this embodiment performs its adaptive interference reduction operations independently for each occurring cardiac event, i.e each occurring ventricular event if the second location signal is the ventricular signal. There is no storage, per se, of coefficients (or coefficient patterns) related to a previous event or to classes of events. Therefore, performance is maintained regardless of changing or variable IEGM morphology, as in the case of alternating ventricular signal shapes, or changes related to heart rate and/or sympathetic drive. Also, for this reason, no special provision is required in conjunction with ventricular paced events, or the occurrence of premature ventricular contractions.

BRIEF DESCRIPTION OF THE DRAWINGS

A better understanding of the invention will be obtained by reference to the appended drawings, wherein identical parts are identified with identical reference numbers and wherein:

FIG. 1 is a schematic representation of a least-mean-squares adaptive Filter according to the present Invention;

FIG. 2a through 2d show a first example of application of the present invention, as applied to a set of electrograms from atrial and ventricular leads;

FIG. 3a through 3d show a second example of application of the present invention, as applied to a set of electrograms from atrial and ventricular leads;

FIG. 7 shows a generalized LMS adaptive filter, written as a Matlab function m-file.

DETAILED DESCRIPTION OF THE INVENTION

Figure 8:
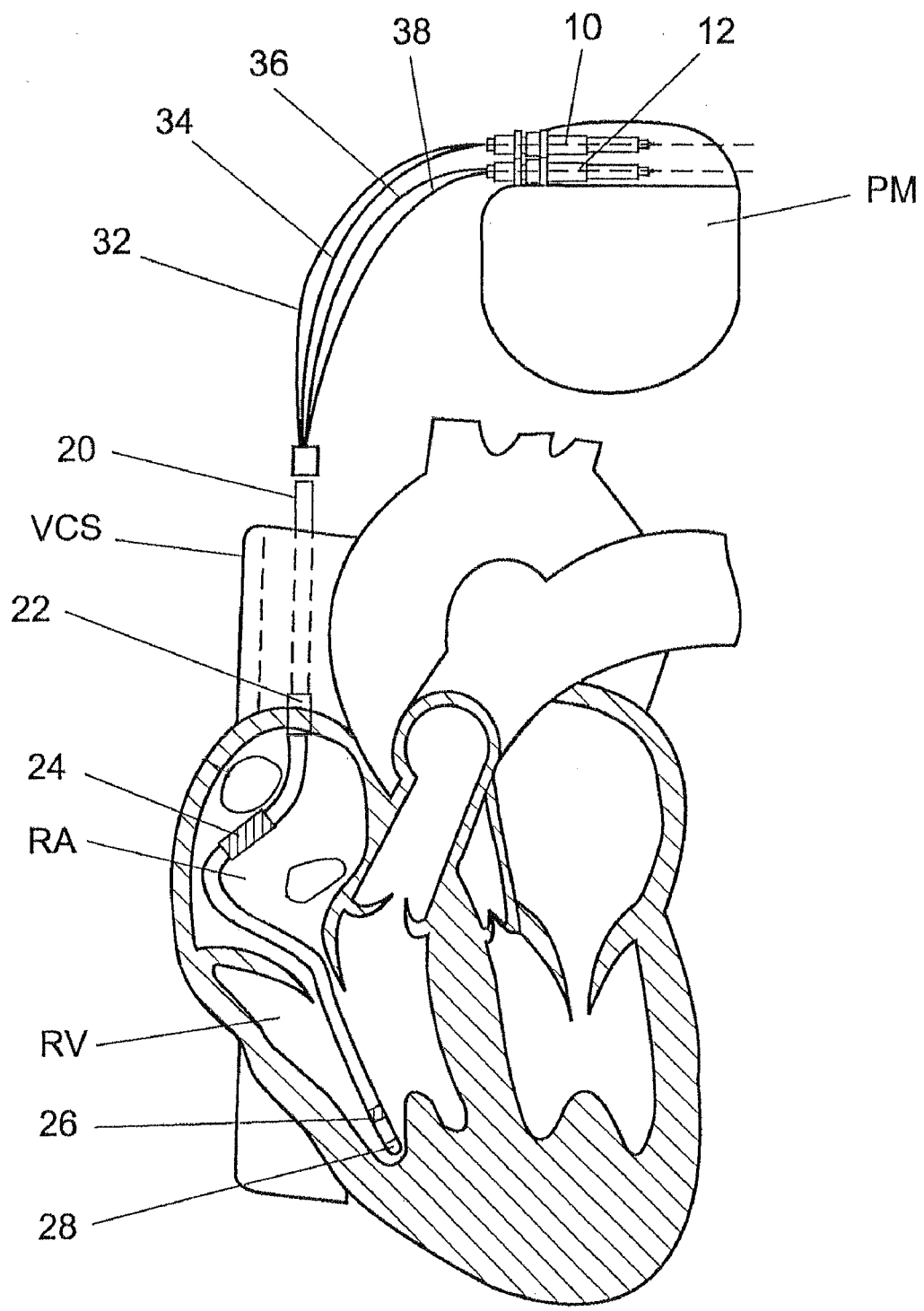
FIG. 8 shows a pacemaker having sensing electrodes in an atrium and a ventricle of a heart

FIG. 8 gives an overview over the environment in which the claimed invention is used. FIG. 8 shows a pacemaker PM with an atrial input connector 10 and a ventricular input connector 12. The pacemaker PM is connected to a pacing and sensing electrode lead 20 having two atrial electrodes 22 and 24 and two ventricular electrodes 26 and 28. The atrial electrodes 22 and 24 are connected to the atrial connector 10 via leads 32 and 34. Likewise, the ventricular electrodes 26 and 28 are connected to the ventricular connector 12 via leads 36 and 38.

The ventricular electrodes 26 and 28 are placed in the apex of the right ventricle RV of a human heart. The atrial electrodes 22 and 24 are placed in the right atrium RA of the human heart. The electrode lead 20 is fed to the right atrium RA and the right ventricle RV via the vena cava superior VCS.

The arrangement shown in FIG. 8 is generally known. With respect to the claimed invention it should be noted, that the atrial electrodes 22 and 24 serve for sensing an atrial intracardiac electrogram. As already pointed out, this atrial intracardiac electrogram not only represents the near-field atrial signal (near-field atrial myocardal potentials) but is additionally influenced by potentials originating from the ventricle which in the atrium are sensed as far-field electrical activities. It is an object of the invention to eliminate the far-field electrical activity sensed in the atrium as far as possible. For this purpose the pacemaker PM comprises an adapted filter compensator as described below.

The present invention applies theoretical principles for reducing signal interference to a particular case involving implanted medical devices. In doing this, it applies the general techniques of adaptive filtering, including the least-mean-squares adaptive filtering technique, to reduce IEGM interchamber or far-field crosstalk. By applying these techniques with adjunct operations, effectiveness of the implanted device is increased and implementation is simplified. Some of the affected adjunct operations include automatic control of the filter adaptation process, pre-processing of the interference reference signal, and accommodating the interference features that may precede the onset of adaptation.

It is to be understood that the techniques of the present invention are applicable to any inter-chamber or far-field interferences encountered in an implanted medical device. However, for purposes of teaching the invention, the description provided will be limited to a single example of interest, that is, the reduction of interference of an atrial IEGM Signal, as sensed by an implanted atrial lead, by far-field crosstalk produced by a ventricular depolarization/repolarization. This latter signal is also available on an implanted ventricular lead as a near-field signal.

In accomplishing the objectives of the invention, the inventors do not blank the atrial channel. Instead, waveform crosstalk artifacts are subtractively removed by an automated process that allows continuous observation of the atrial waveforms.

One way of accomplishing this goal is presented in FIG. 1, which shows a configuration of an adaptive filter using the least-mean-squares (LMS) algorithm. This particular algorithm is known and is employed to reduce the effects of interference on a received signal, in cases where it is feasible to approximately model the potentially interfering signal.

The block diagram of FIG. 1 shows that the adaptive filter comprises several parts. The first of these is a first input signal port that receives an input signal that includes the "desired" signal, which is the first location (atrial) sensed signal potentially affected by (ventricular) far field signals. The first input port is connected to an L/2-stage delay block, in order to assure realizable (causal) filter coefficients. The N/2-stage delay block in the input-signal channel introduces a short processing delay, equivalent to that number of signal samples, and will be in the neighborhood of 30 milliseconds, depending on system parameters. This is required to assure that signals from the desired input signal port do not precede signals from the FIR filter output, as seen at the subtraction (difference) block, thus meeting the causality requirements of the coefficient update algorithm disclosed in further detail further below.

There also is provided second input port, referred to as an interference-reference input port, which receives a second location sensed signal, e.g. a (near field) ventricular signal as an input signal for an adaptive filter, referred to as the interference reference signal. This second input port is connected to an adaptive filter which generates an estimate of the interference affecting the desired signal and the potentially interfering signal. The adaptive filter is a finite-impulse-response (FIR) filter that operates based upon adjustable coefficients. Also providing input to the adaptive filter is a module for adjusting the filter coefficients of the finite-impulse-response (FIR) filter. In the particular case being illustrated, the module for adjusting the filter coefficients is a LMS algorithm module.

An output of the L/2-stage delay block and an output of the L-stage FIR filter each serve as inputs to a subtraction module, where a difference of the inputs is generated. This difference serves as both a filtered output signal from the adaptive filter and as an error signal to be fed back to the adjusting means as an input thereto.

The adaptive filter of FIG. 1 may be summarized as a filter where the adjusting algorithm adjusts the filter to minimize the error signal, thereby reducing the second location interference contained in the first location input signal. In the method taught herein, the algorithm is a least-mean-squares algorithm that uses a "steepest-descent" search strategy an a multi-dimensional error surface. Efficient computational methods for this strategy are known and are described in texts such as "Statistical Digital Signal Processing and Modeling" by Monson Hayes, published by John Wiley & Sons (New York, 1996) and "Adaptive Filter Theory", third edition, by Simon Haykin, published by Prentice-Hall, Inc. (Upper Saddle River, NI, 1996).

An application of present invention is now provided as FIG. 2a through 2d. FIG. 2a is an example of an atrial IEGM signal that has been seriously corrupted by additive crosstalk from the adjacent ventricular chamber. FIG. 2b shows an estimate of the ventricular signal causing the crosstalk of FIG. 2a. It has been derived, as described in more detail below, from the actual near-field ventricular IEGM signal, which is not shown. FIG. 2a and the actual near-field ventricular IEGM signal are taken from Patient File z141448, distal HRA-Bi and distal RVA-Bi leads, Ann Arbor Electrogram Libraries, Ann Arbor, Mich.

There are several aspects of this example situation which bear notation.

First, the ventricular interference signal is of relatively short duration, as opposed to being more random and/or continuous. It may be uniquely established by sensing the waveform in a near-field ventricular lead, which would usually be present in the implanted medical device to support other basic functions, if for no other reason. Because of this, the ventricular signal itself or a marker signal derived from the ventricular signal may be used as a trigger signal for a gate to activate the LMS filter adaptation process only if ventricular event (QRS complex) occurs. Activation of the LMS filter adaptation process is not needed to operate when the related interference signal is not present. Once activated, the adaptation process operates for a predetermined interval, which is selected to be slightly longer than the expected duration of the crosstalk interference detected in the atrial channel by the atrial lead. When adaptation is not enabled, the FIR filter coefficients are set to zero, and the algorithm has no effect on the desired (in this example, atrial) signal.

Second, the onset of far-field crosstalk interference may slightly precede the near-field sensing of the ventricular event, as is noted by a comparison of FIGS. 2a and 2b at common times, that is, by drawing a vertical line down through the respective figures when they are aligned as to time. This slight precedence in the far-field, that is, atrial, sensing of the event may be due to a variety of factors, including variations in implant lead placement, cardiac tissue geometry, and the actual pathway of the ventricular event wavefront. This precedence effect may be effectively minimized by using an adaptive FIR filter structure of sufficient length to include the expected preactivation interference. When this is done, the means for adjusting the filter coefficients will automatically position the set of LMS-based FIR coefficients within the structure, achieving the desired interference reduction.

Third, the effectiveness of an LMS adaptive filter will depend strongly upon how realistic the noise reference signal is, compared to the actual interference. In other words, there is a need for the noise reference to be highly correlated to the actual interference, but less strongly correlated with the desired signal, for the LMS algorithm to perform effectively. When that happens, the FIR filter adaptation can achieve an accurate subtraction of the interfering waveform. In the particular circumstance of attempting to reduce IEGM ventricle-to-atrium inter-chamber crosstalk in an application of the invention to an implanted medical electrotherapy device, this means that an obvious choice for the noise reference signal to be input to the L-stage FIR filter is the ventricular IEGM signal itself. As already noted, this signal is generally readily available from an implanted ventricular lead, providing a localized "near-field" view of the passage of the ventricular event wavefronts, whether they are depolarizations or repolarizations. However, when observed as interference in the far-field setting of an atrial lead, the signal will be incidentally filtered by the geometry and behaviour of intervening quasi-parallel conductive pathways. The crosstalk interference will therefore be prolonged in duration and have relatively diffused waveform transitions. This is clearly shown in FIGS. 2a and 2b by comparison of the respective signals. Accordingly, it is advantageous to pre-process the near-field ventricular waveform before it is used, to improve the correlation of the noise reference signal to the expected far-field interference. One way to achieve this is by using a fixed-coefficient FIR filter of suitable design. In conducting simulations of this technique, the inventors have noted that a simple moving-average filter can significantly improve the interference reduction. Advanced implementations may employ other preprocessing methods, using adaptive (but slowly-varying) coefficients as appropriate.

For these reasons, the waveform shown in FIG. 2b is not the actual near-field ventricular signal, but is instead a first estimate of the far-field interference derived from the actual near-field ventricular signal.

Turning now to FIG. 2c, the benefit of using the invention in the waveforms of FIG. 2a and the derived waveform of FIG. 2b is illustrated as a post-processed atrial signal, that is, as the output signal of the filter block of FIG. 1. This post-processed atrial signal was generated using a Matlab/Simulink system simulation described in more detail below.

Finally, FIG. 2d shows the enabling signal used in the Matlab/Simulink simulation for LMS filter adaptation. This signal is triggered from the near-field ventricular IEGM signal, which, as previously noted, is not shown.

While the preceding example shows the efficacy of the inventive technique, it does not fully portray the advantages of the invention over the known blanking techniques. Particularly, the preceding example does not show how the inventive technique permits the detection of an atrial event that is concurrent with a ventricular event that is causing interference in the atrial signal. However, the advantage of the present invention may be seen by reference to FIG. 3a through 3d.

Because of similarities in the content of FIG. 3a through 3d to FIG. 2a through 2d, it is not necessary to describe the contents in as much detail.

However, it is noted that a brief, artificial atrial-channel event has been incorporated into FIG. 3a. This atrial-channel event is incorporated during the duration of the expected crosstalk interference. If the known blanking technique was being employed in this instance, the activation of the blanking protocol in the atrial signal channel would prevent this brief event from being observed. However, when the same type of far-field ventricular estimate of FIG. 3b is prepared and applied using the adaptive filter, using an enabling signal according to FIG. 3d, the same Matlab/Simulink technique provides a post-processed atrial signal according to FIG. 3c. As expected, the continuous reception of the atrial signal, even during expected crosstalk intervals, results in the previously unknown capacity to detect the brief, artificial atrial-channel event.

Figure 4:
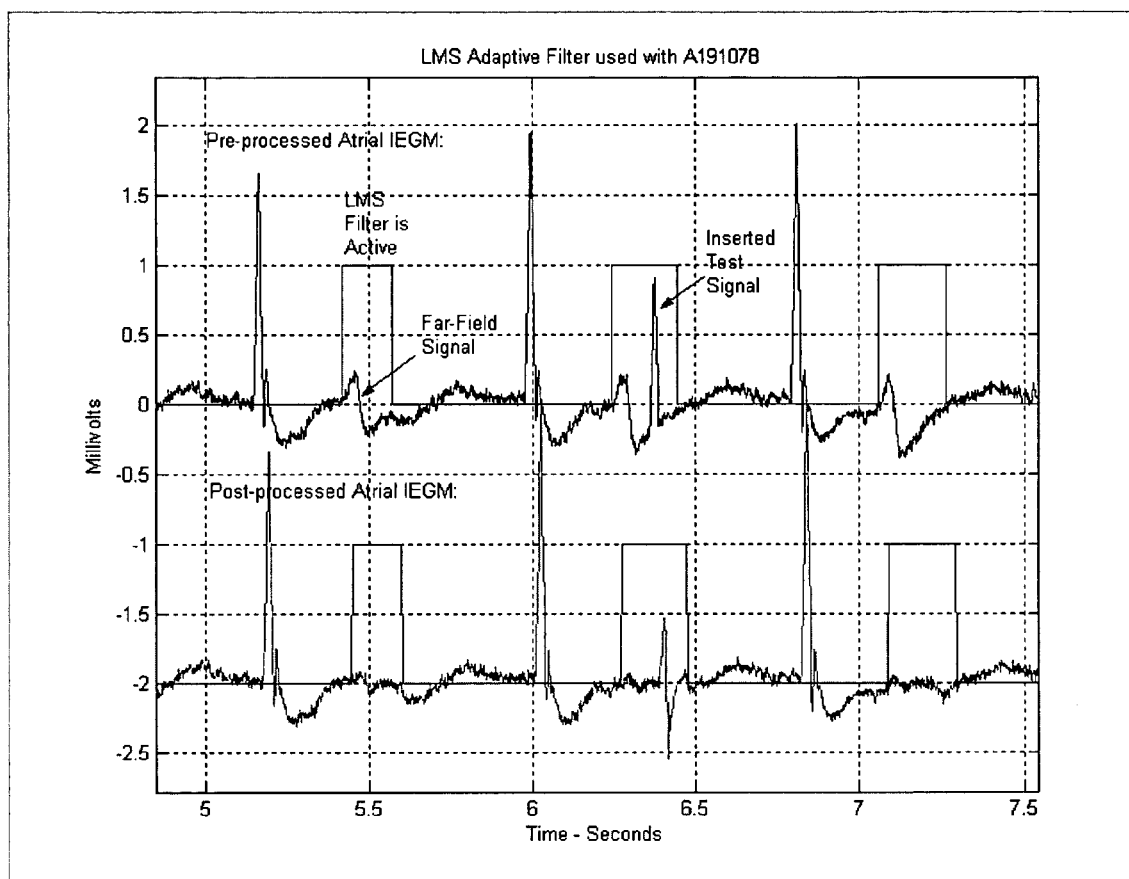
FIG. 4 is an electrogram that shows another example of far-field interference reduction using the principles of the invention.

FIG. 4 shows another example of far-field interference reduction using these principles [Ann Arbor Electrogram Libraries, Ann Arbor Mich.: Patient file A191078, distal HRA-Bi and distal RVA-Bi leads]. Three cardiac cycles of atrial IEGM data are included; in the second of these, an artificial atrial test signal has been positioned within the filter adaptation interval. The post-processed signal, as would be seen at the "Basic Output" port of FIG. 1, shows that reduction of crosstalk by means of the adaptive filter does not remove or conceal a co-existing atrial event. That is, during the time that filter adaptation (hence, noise reduction) is active, the output includes this atrial test signal, which however now appears in first derivative form.

If the desired input waveform must be accurately represented during active intervals of the noise reduction process, a Morphology Restoration (MR) block may be added to the overall system, as shown in FIG. 1. In that case, the "Enhanced Output Signal" port would be used. The MR block functions as a gated integrator; its output simply tracks the basic output signal while filter adaptation is OFF, but sums the basic output signal values to its output whenever filter adaptation is ON. In this manner, the first-derivative transformation of the (active) noise reduction algorithm may be avoided.

Figure 5:
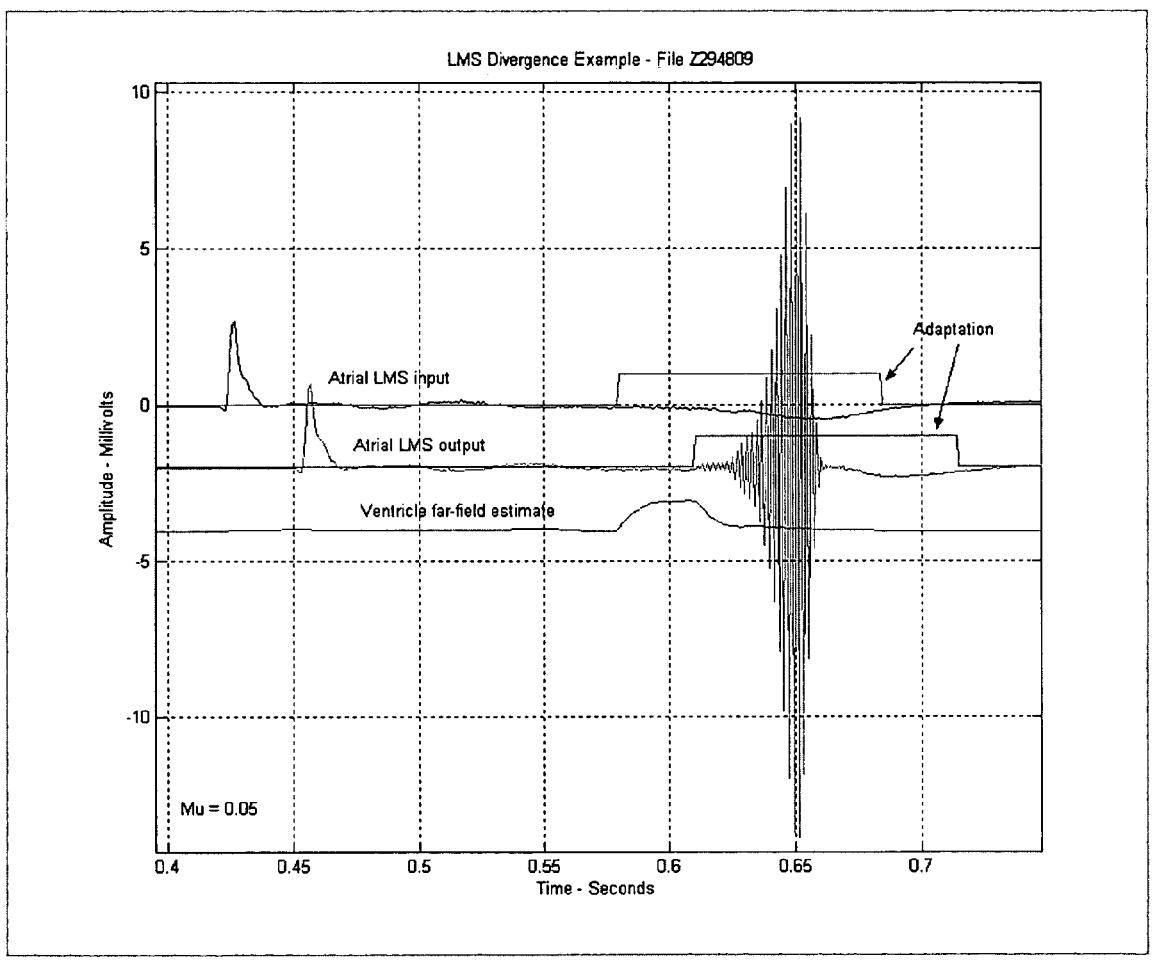
FIG. 5 is an electrogram that shows that, without normalization, data-dependent instabilities can occur.
Figure 6:
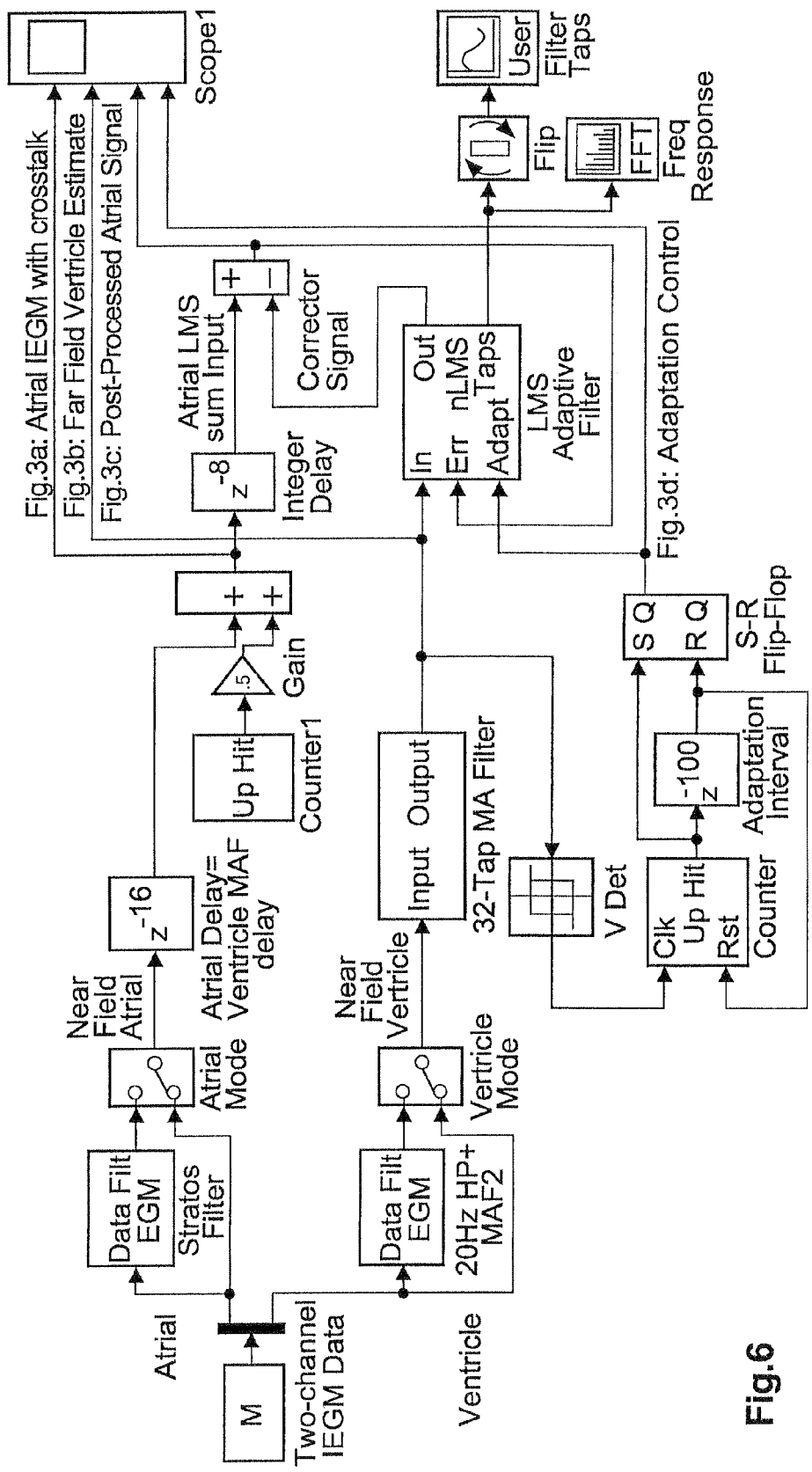
FIG. 6 shows a schematic representation of the Matlab/Simulink simulation diagram used in the examples.

Of particular benefit is the use of step size normalization within the filter coefficient update algorithm. For the LMS algorithm, this feature guarantees stable behavior for a known range of parameter values ($0<\mu<2$), independent of the input data statistics. Without normalization, data-dependent instabilities can occur, as shown in FIG. 5. In the case of an LMS adaptive filter, normalization is provided by the summation term in the denominator of the update algorithm, as shown in FIG. 1. Without normalization, the denominator is simply unity. Implementing this normalized least-mean-square (NLMS) sum-of-squares algorithm requires a minimum of one additional multiply, divide, and addition (per coefficient) over the standard LMS algorithm for shift-input data. The computational workload associated with this may, if necessary for an implant application, be reduced by several alternative methods, including but not limited to the following three:

A first alternative uses a normalization based on k [max $(X)]^2$, where $k<L$ is an integer constant, chosen to provide an upper bound to the sum-of-squares method. This avoids squaring each data value.

Characterization of IEGM data types allows proper selection of parameter k; the system may include algorithm divergence sensing.

A second alternative uses a modified update algorithm, such as the computationally efficient form proposed by Nagumo & Noda, for which:

$$W_{k+1} = W_k + \mu \frac{e_k \, \text{sgn}(X_k)}{\sum_{m=1}^{L} |x_{m,k}|}$$

This uses only the sign of the data in FIR filter memory, with normalization based on the sum of the data absolute values. As a result, multiplication workload is greatly reduced.

A third alternative uses the Douglas update algorithm, whereby the only filter coefficient updated at time k is that associated with the largest data sample currently in filter memory:

$$w_{i,k+1} = \begin{cases} w_{i,k} + \mu \dfrac{e_k}{x_{i,k}}, & \text{if } |x_{i,k}| = \max_{1 \le i \le L} |x_{j,k}| \\ w_{i,k}, & \text{otherwise.} \end{cases}$$

in the above examples for deriving the figures associated with the examples described above.

FIG. 7 shows a code listing, written as a Matlab function m-file, for generating a generalized LMS filter, as used in association with the above examples to derive the figures associated therewith.

Accordingly, from the foregoing description, it may be inferred that the invention relates to the technique of using an LMS adaptive filter to effectively reduce inter-chamber IEGM far-field interference within an implanted medical device, particularly when simpler methods of IEGM interpretation yield ambiguous or incomplete results. Further, the invention relates to a technique where the LMS filter adaptation is activated only when interfering signal events occur. This allows the computational burden on the implanted medical device to be reduced. Yet further, the invention relates to a technique that includes pre-processing the interfering signal, as observed, for example, in a near-field cardiac lead, especially a ventricular lead, to cause it to resemble the interference signal as it will be expected to be observed in the far-field cardiac lead, that is, for example, in an atrial lead. This pre-processing occurs prior to the ventricular lead signal being applied to the LMS adaptive filter as an input signal. And still further, the invention relates to the inclusion of a finite-impulse-response (FIR) filter of sufficient length into the filter to effectively adapt to the situation where the interference signal from the triggering waveform will be detected in the far-field lead prior to being detected in the near-field lead, This enables the adaptation process to manage preactivation events. Finally, the invention relates to an implanted medical device having the inventive technique incorporated within it.

The methods of this invention may be implemented by computer software, running on a microprocessor appropriate for digital signal processing tasks. Alternatively, they may be implemented by means of a dedicated VLSI structure, incorporating gates, registers, and the like, to perform the required functions. It is expected that the latter approach would provide the most efficient operation for use in medical implant devices.

The invention claimed is:

1. An implantable medical device comprising:
   at least two sensing channels for receiving sensed first and second location electrical signals originating from two different locations of a heart;
   a control unit connected to said sensing channels and being adapted to process the sensed electrical signals originating from the first and second locations of the heart,
   wherein the control unit incorporates an adaptive filter compensator adapted to generate an estimate signal for compensating a far-field contribution of the second location signal to the first location signal, and adapted to generate an output signal representing a near field signal originating from the first location using said estimate signal to reduce inter-chamber interference; and
   a gate connected to the second location sensing channel and being adapted to enable the adaptive filter compensator only if a predetermined signal is sensed via the second location sensing channel;
   wherein the device includes a morphology restoration block to restore an original morphology of the first location sensed after any said inter-chamber interference encountered in the implantable medical device is reduced by the adaptive-filter compensator; and
   wherein the morphology restoration block includes an on/off switchable integrator, said integrator being adapted so that the integrator's output tracks the output signal while the adaptive filter compensator is not enabled, but sums the basic output signal values to the integrator's output whenever the adaptive filter compensator is enabled.

2. The implantable medical device according to claim 1, wherein the gate is adapted to enable the adaptive filter compensator for a predetermined period of time.

3. The implantable medical device according to claim 1, wherein the adaptive filter compensator comprises an L-stage least mean square adaptive filter.

4. The implantable medical device according to claim 1, wherein the first location electrical signal is an atrial signal and the first sensing channel is an atrial sensing channel.

5. The implantable medical device according to claim 4, wherein the first sensing channel is adapted to be connected to an intracardiac electrode lead having an atrial sensing electrode to be placed in an atrium of a heart.

6. The implantable medical device according to claim 1, wherein the second location electrical signal is a ventricular signal and the second sensing channel is a ventricular sensing channel.

7. The implantable medical device according to claim 6, wherein the second sensing channel is adapted to be connected to an intracardiac electrode lead having a ventricular sensing electrode to be placed in a ventricle of a heart.

8. The implantable medical device according to claim 4, wherein the far-field contribution of the second location signal to the first location signal to be compensated is a far-field QRS signal originating from a ventricle and is sensed via the atrial channel and that the adaptive filter compensator is adapted to generate a compensation signal being approximately inverse to the far-field QRS signal sensed via the atrial channel.

9. The implantable medical device according to claim 1, wherein the adaptive filter compensator has an input for an a noise reference input signal to be processed for generating the compensation signal, said noise reference input signal being a ventricular sensing signal.

10. The implantable medical device according to claim 1, wherein the device comprises a preprocessor for preprocessing a noise reference input signal prior to processing by the adaptive filter compensator.

11. The implantable medical device according to claim 10, wherein the preprocessor for preprocessing noise reference input signal comprises a fixed coefficient finite impulse response (FIR) filter.

12. The implantable medical device according to claim 1 further comprising a filter coefficient updater comprising a step size normalizer and, wherein the adaptive filter compensator comprises an L-stage least mean square filter which is connected to the filter coefficient updater.

13. The implantable medical device according to claim 1, wherein the control unit is adapted to determine for each actual event in the second location sensed signal a new set of actual coefficients determining the operation of the adaptive filter compensator.

14. The implantable medical device according to claim 6, wherein the far-field contribution of the second location signal to the first location signal to be compensated is a far-field QRS signal originating from a ventricle and is sensed via the atrial channel and that an adaptive filter compensation means is adapted to generate a compensation signal being approximately inverse to the far-field QRS signal sensed via the atrial channel.

* * * * *